United States Patent [19]

Sano et al.

[11] Patent Number: 4,861,722
[45] Date of Patent: Aug. 29, 1989

[54] CORYNEFORM BACTERIA CARRYING RECOMBINANT PLASMIDS AND THEIR USE IN THE FERMENTATIVE PRODUCTION OF L-LYSINE

[75] Inventors: Konosuke Sano, Tokyo; Koichi Ito, Kawasaki; Kiyoshi Miwa, Matsudo; Shigeru Nakamori, Yokohama, all of Japan

[73] Assignee: Ajinomoto Company, Inc., Tokyo, Japan

[21] Appl. No.: 56,310

[22] Filed: Jun. 1, 1987

Related U.S. Application Data

[63] Continuation of Ser. No. 525,993, Aug. 24, 1983, abandoned.

[51] Int. Cl.[4] ............................................. C12N 1/20
[52] U.S. Cl. ........................... 435/252.32; 435/115; 435/172.1; 435/172.3; 435/320; 435/840; 435/843; 935/29; 935/61
[58] Field of Search .................. 435/115, 172.1, 172.2, 435/253, 232, 317, 840, 843; 935/14, 27, 29, 59–61

[56] References Cited

U.S. PATENT DOCUMENTS

| | | | |
|---|---|---|---|
| 4,346,170 | 8/1982 | Sano et al. | 435/115 |
| 4,411,977 | 10/1983 | Shimazaki | 435/115 |
| 4,442,208 | 4/1984 | Tsuchida | 435/116 |
| 4,452,980 | 6/1984 | Tsuchida | 435/115 |
| 4,514,502 | 4/1985 | Miwa et al. | 435/843 |
| 4,560,654 | 12/1985 | Miwa | 435/115 |

FOREIGN PATENT DOCUMENTS 2482622  11/1981  France ............................. 435/115

OTHER PUBLICATIONS

Chenais et al., "Construction of Hybrid Plasmids Containing the Lys A Gene of *Escherichia coli*" Studies of Expression in *E. coli* and *Saccharomyces cerevisiae*, Chem. Abstracts vol. 95, p. 331 (1981) #146961x.

*Primary Examiner*—Margaret Moskowitz
*Attorney, Agent, or Firm*—Oblon, Fisher, Spivak, McClelland & Maier

[57] ABSTRACT

A genetic sequence coding for the production of a protein having the activity of diaminopimelic acid decarboxylase and having two Pst I cleavage sites in its DNA chain and a molecular weight of 2.9±0.05 Md, is incorporated into a vehicle capable of replication in Coryneform bacteria and used to produce L-lysine by fermentation.

9 Claims, 8 Drawing Sheets

CORYNEFORM BACTERIA CARRYING RECOMBINANT PLASMIDS AND THEIR USE IN THE FERMENTATIVE PRODUCTION OF L-LYSINE

This application is a continuation of application Ser. No. 06/525,993, filed on Aug. 24, 1983, now abandoned.

BACKGROUND OF THE INVENTION

1. Field of the Invention

The present invention relates to Coryneform bacteria containing plasmids made by recombinant DNA techniques carrying genetic information useful for the fermentative production of lysine.

2. Description of the Prior Art

L-lysine, which is used as a feedstuff, is normally produced industrially by a fermentation process in which L-lysine producing mutants of the genus Brevibacterium or Corynebacterium are used. Various L-lysine-producing mutants, produced by the artificial mutation of wild strains of microorganisms of the genera Brevibacterium and Corynebacterium, are known. Examples of such artificial mutants are mutants resistant to S-(2-aminoethyl)-cysteine (hereinafter identified as AEC), mutants requiring L-amino acids such as L-homoserine for their growth (Japanese Published Examined Patent Application Nos. 28078/1973, 6499/1981), mutants resistant to AEC and further requiring an amino acid such as L-leucine, L-homoserine, L-proline, L-serine, L-arginine, L-alanine or L-valine, (U.S. Pat. Nos. 3,708,395 and 3,825,472), L-lysine-producing mutants resistant to DL-α-amino-ε-caprolactam, α-amino-lauryllactam, aspartic acid-analogues, sulfa drugs, quinoids, N-lauroyl leucine, or to inhibitors of oxalacetate, decarboxylase or respiratory system enzymes (Japanese Published Unexamined Patent Application Nos. 53588/1975, 31093/1975, 102498/1977, 9394/1978, 86089/1978, 9783/1980, 9759/1980, 32995/1981, 39778/1981, Japanese Published Examined Patent Application Nos. 43591/1978, 1833/1978), L-lysine-producing mutants requiring inositol or acetic acid (Japanese Published Unexamined Patent Application Nos. 9784/1980, 8692/1981), and L-lysine-producing mutants sensitive to fluoropyruvic acid or to temperatures higher than 34° C. (Japanese Published Unexamined Patent Application Nos. 9783/1980, 86090/1978). Copending, coassigned U.S. patent application Ser. No. 333,455, now U.S. Pat. No. 4,411,977 filed Dec. 22, 1981, discloses a mutant of Brevibacterium or Corynebacterium which is resistant to ethylene glycol and which produces L-lysine.

The prior art has described *Escherichia coli* strains transformed with a recombinant plasmid DNA, which strains have increased productivity of amino acids (see, for example, U.S. Pat. No. 4,278,765).

Although the presence of plasmids in strains of Brevibacterium and Corynebacterium having detectable phenotypic markers has not been known for a long time (but see, e.g., Published European Patent Application No. 003391), recent work has demonstrated the feasibility of preparing Coryneform bacteria harboring plasmids controlling the production of threonine or isoleucine see the commonly assigned, Ser. No. 376,396 now U.S. Pat. No. 4,452,890 copending at the U.S. Patent and Trademark Office, filed May 10, 1982 (thr), and commonly assigned copending Ser. No. 392,145, now U.S. Pat. No. 4,442,208 filed June 25, 1982 at the U.S. Patent and Trademark Office (ile)). In addition, commonly asigned copending U.S. patent application Ser. No. 386,980, now U.S. Pat. No. 4,514,502 filed on June 10, 1982 at the U.S. Patent and Trademark Office, describes composite plasmids capable of propagating in Coryneform glutamic acid producing bacteria. (All of these patent applications are herein fully incorporated by reference.)

A brief schematic representation of the lysine, isoleucine and threonine biosynthetic pathway is as follows:

Scheme I

The first branch of the pathway leading to threonine and isoleucine can be found at the junction of aspartate semialdehyde. The enzyme leading to these two amino acids is homoserine dehydrogenase (hereinafter "HDase"), while the enzyme leading to lysine is dihydrodipicolinate synthetase, ("DHDP synthetase").

It should also be noted here that, recently, *Escherichia coli* strains were described which carry hybrid plasmids containing several genes of the lysine biosynthetic pathway. An overproducer of lysine (TOC R 21) was transformed, and the synthesis of lysine was studied in different strains (see, for example, (LeReverend at al, European Journal of Applied Microbiology and Biotechnology, 15: 227–231 (1982), as well as published French Patent Application No. 2511032 (Application No. 81/15385) published Feb. 11, 1983. It appears from these publications that only plasmids containing the dapA gene (encoding DHDP synthetase) lead to an increase in lysine production; this reaction is the limiting biosynthetic step in lysine overproducers (having mutations altering the aspartokinase reaction). The authors suggest that such a method of gene amplification could be used to improve strains which overproduce metabolites. There is no suggestion in these publications, however, to expand this work to Cornyeform bacteria. Commonly assigned copending U.S. application, Ser. No. 504,471, now U.S. Pat. No. 4,601,983 filed on June 15, 1983, discloses recombinant plasmids carrying genetic information to control isoleucine and threonine biosynthetic pathways, present in Cornyeform bacteria.

A need still exists for improved and efficient methods for the fermentative production of L-lysine.

SUMMARY OF THE INVENTION

The inventors have discovered that when the genetic information coding for diaminopimelic acid decarboxylase (DAPDase) is combined into an appropriate vehicle capable of replication in Coryneform bacteria, and the resulting hybrid vehicle carrying said genetic information is replicated in an appropriate Coryneform bacterium host or recipient, the transformed Coryneform microorganism is an excellent producer of L-lysine. This invention is of particular interest since many strains of Brevibacterium and Corynebacterium genera within the Coryneform type producing high amounts of L-lysine can be utilized as hosts.

The invention thus relates to a process for the fermentative production of L-lysine, and to the various genetic and microbiological elements involved in said process. For example, the invention relates to the isolated form of the gene for diaminopimelic acid decarboxylase, to various vehicles containing said gene, which vehicles are replicable in Coryneform bacteria, to various microbes of the Coryneform type containing such vehicles, and to various fermentation processes for the production of L-lysine.

DESCRIPTION OF THE PREFERRED EMBODIMENTS

The biosynthetic pathway for the production of lysine, threonine and isoleucine is shown in the "Description of the Prior Art". The scheme demonstrates the presence of DAPDase enzyme as the last step in the branch leading to L-lysine. DNA containing sufficient genetic information to code for DAPDase is obtained from an appropriate DNA donor. Preferably, the donor is a Coryneform bacterium, most preferably *Brevibacterium lactofermentum*. The genetic information coding for DAPDase can be obtained by partial digestion of DNA from the donor, introduction of the genetic sequence into an appropriate plasmid, transformation of an DAPDase deficient Coryneform bacteria with the resulting mixture of recombinant DNAs, and isolation of transformants which can grow on diamino pimelic acid (dap).

In particular, the DAPDase genetic information-containing sequence may be obtained from *Brevibacterium lactofermentum* ATCC 13869 (wild type). The genetic information comprising the DAPDase gene can be found in a DNA fragment having a molecular weight of about 2.9±0.1 megadaltons, having two Pst I, two Sac I, two Hind III, one Cla I restriction endonuclease sites, and being flanked by two Pst I sites.

The recipients or hosts useful for the transformation are the so-called Coryneform bacteria. These are aerobic, Gram positive rods, non acid fast, and are described in Bergey's Manual of Determinative Bacteriology, 8th Edition, 599 (1974). Examples of specimens of wild strains of Coryneform bacteria useful as hosts in the invention are as follows:

*Brevibacterium divaricatum* ATCC 14020,
*Brevibacterium saccarolyticum* ATCC 14066,
*Brevibacterium immariophilum* ATCC 14068,
*Brevibacterium lactofermentum* ATCC 13869,
*Brevibacterium roseum* ATCC 13825,
*Brevibacterium flavum* ATCC 13826,
*Brevibacterium thiogenitalis* ATCC 19240,
*Corynebacterium acetoacidophilum* ATCC 13870,
*Corynebacterium acetoglutamicum* ATCC 15806,
*Corynebacterium callunae* ATCC 15991,
*Corynebacterium glutamicum* ATCC 13032, 13060,
*Corynebacterium lilium* ATCC 15990,
*Corynebacterium melassecola* ATCC 17965, and others.

A preferred result may be obtained when the Coryneform bacteria are mutated in a known manner to a lower restriction enzyme activity prior to using them as the hosts.

When the Coryneform bacteria are transformed with vehicles carrying the DAPDase insert, they then express the genetic information possessed by the foreign gene.

Of particular interest are hosts which are either auxotrophs for homoserine dehydrogenase or are resistant to S-(2-aminoethyl)-cysteine (AEC). Hosts that are prototrophic in DAPDase are also preferred. Insertion thereinto of a gene coding for DAPDase, especially in a multicopy plasmid, greatly increases the number of gene copies for this enzyme, and greatly increases the production of final L-lysine. In fact, the highest concentrations of L-lysine may be obtained by the use of multicopy plasmids carrying the DAPDase gene in a DAPDase prototrophic (DAPDase+) host. Auxotrophs for DAPDase are usually used as the hosts for selection and isolation of the vehicles carrying the DAPDase gene. It is then convenient to use the thus isolated vehicle for the transformation of prototrophs for DAPDase.

Also of interest is the use of either aspartokinase wild hosts, or hosts which have been mutated by altering the aspartokinase reaction. In hosts herein the aspartokinase reaction has been mutated so that the hosts overproduce lysine, the aspartokinase reaction is no longer rate limiting. The maximum effect can thus be obtained by utilizing such a mutated host.

Any replicable vehicle, capable of replication in Coryneform bacteria can be utilized to carry the DAPDase gene into, and be used for the transformation of the hosts. Vehicles such as plasmids, phages or other vectors can be utilized. Of particular importance are the composite plasmids disclosed in copending Ser. No. 386,980, now U.S. Pat. No. 4,514,980 filed at the U.S. Patent and Trademark Office on June 10, 1982. These plasmids comprise (A) a drive unit region derived from a plasmid (a) capable of propagating in Coryneform glutamic acid producing bacteria, and (B) a gene fragment or fragments derived from a plasmid (b) capable of propagating in *Escherichia coli* or *Bacillus subtilis*, and having at least a region to express resistance to a drug. When the gene fragment additionally carries a drive unit region of plasmid (b), the composite plasmid becomes capable of propagating in *Escherichia coli* or

*Bacillus subtilis*, and thus it can be screened or amplified in *Escherichia coli* or *Bacillus subtilis*.

By the terms "resistance to a drug" is meant to imply resistance to a drug such as an antibiotic which inhibits the growth of a host cell. Examples of such antibiotics are penicillin, kanamycin, chloramphenicol, erythromycin, actinomycin, and the like.

Figure 1:
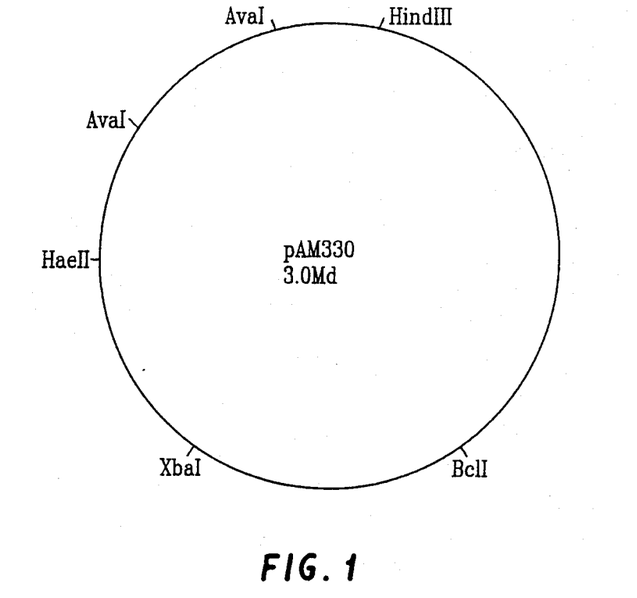
FIG. 1 shows a restriction map of plasmid pAM 330.
Figure 2:
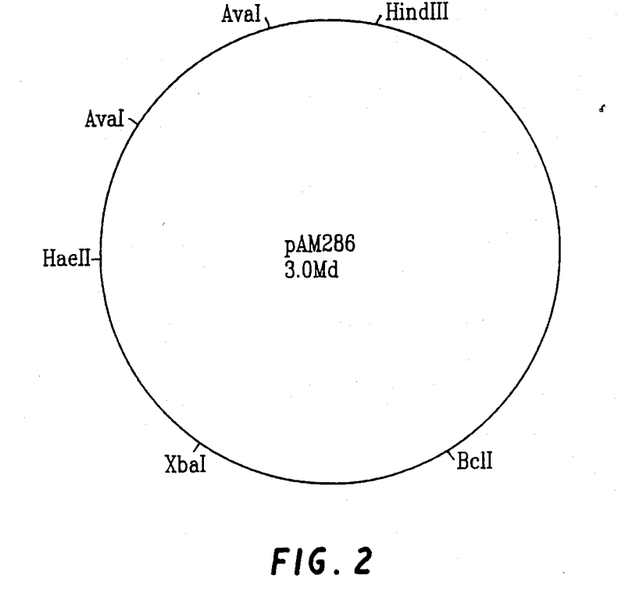
FIG. 2 shows a restriction map of plasmid pAM 286.
Figure 3:
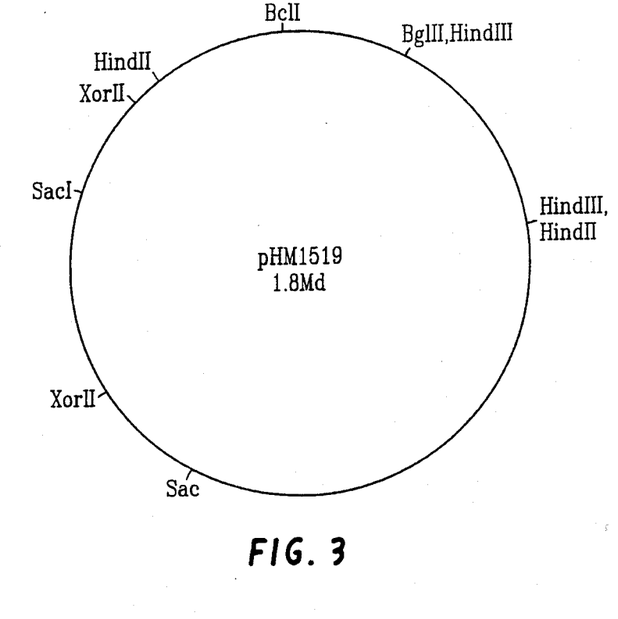
FIG. 3 shows a restriction map of plasmid pHM 1519.

Specimens of multicopy plasmids (a) capable of propagating in Coryneform bacteria are shown in the aforementioned application, and include pAM 330, separated from *Brevibacterium lactofermentum* ATCC 13869, having a molecular weight of 3.0 megadalton (restriction map in FIG. 1), pAM 286 separated from Corynebacterium glutamicum FERM-B 5485, having a molecular weight of 3.0 megadalton (restriction map in FIG. 2), and pHM 1519 separated from *Corynebacterium glutamicum* ATCC 13058, having a molecular weight of 1.8 megadalton (restriction map in FIG. 3).

Plasmids (b) capable of propagating in *Escherichia coli* are multicopy plasmids and have genetic information of resistance to a drug. They are, for example, pAC 105, pBR 322, pBR 324, pBR 325, and the like. Plasmids (b) capable of propagating in *Bacillus subtilis* and having genetic information of resistance to a drug are preferably multicopy, and include pT 127, pC 194, pC 221, pC 223, pUB 110 and the like.

In order to construct the composite plasmid from the plasmids (a) and (b), conventional methods can be employed such as digestion with restriction enzymes, and ligation with ligases.

After the ligation reaction, the desired composite plasmids are screened by isolating plasmids which can propagate in Coryneform bacteria, and can transform the Coryneform bacteria into drug resistance. A composite plasmid having a drive unit region derived from plasmid (a) and another drive unit region derived from plasmid (b), and the drug resistance genes of plasmid (b) can be found among plasmids which can propagate in Coryneform bacteria and *Escherichia coli* or *Bacillus subtilis*, and which can transform the (1) Coryneform bacteria or (2) *Escherichia coli* (in the case where a plasmid was used capable of propagating in *Escherichia coli*), or *Bacillus subtilis* (in case where a plasmid was capable of propagating in *Bacillus subtilis*), and which are drug resistant.

Figure 4:
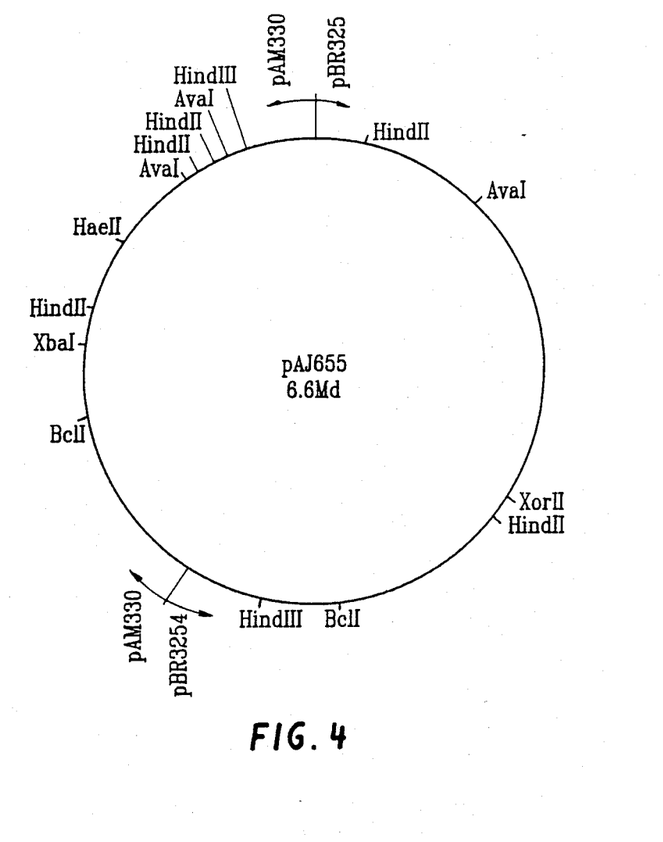
FIG. 4 shows a restriction map of composite plasmid pAJ 655.
Figure 5:
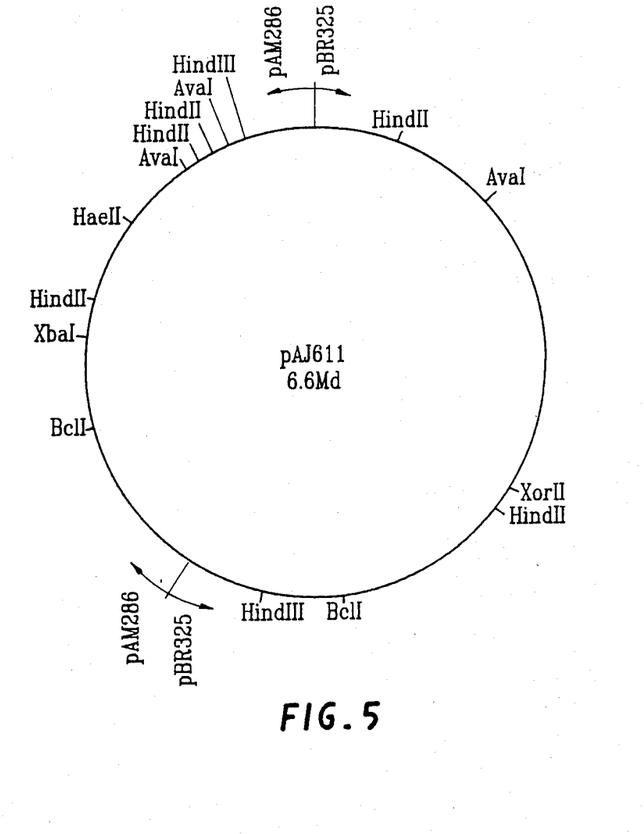
FIG. 5 shows a restriction map of composite plasmid pAJ 611.
Figure 6:
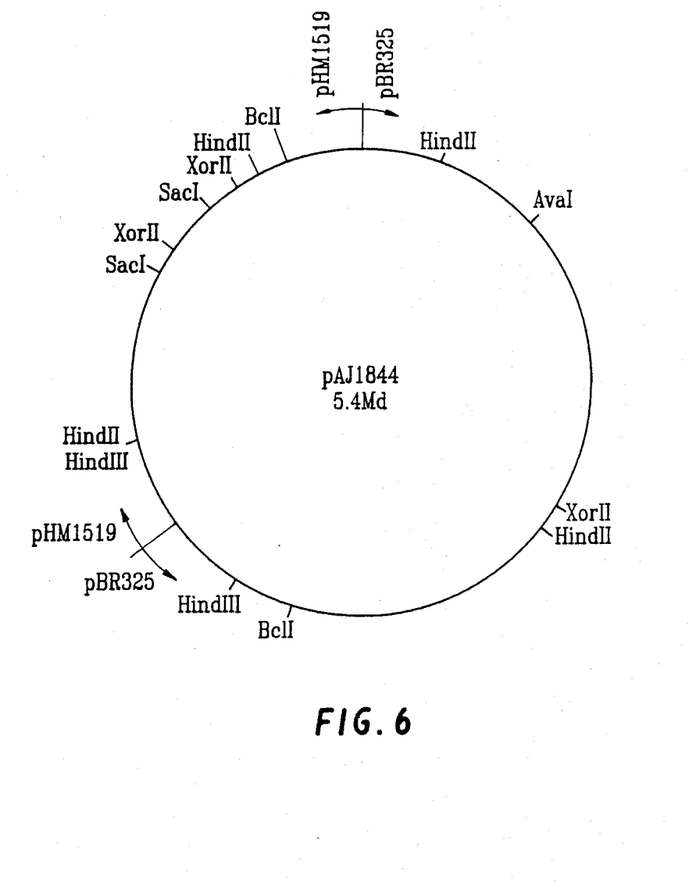
FIG. 6 shows a restriction map of composite plasmid pAJ 1844.
Figure 7:
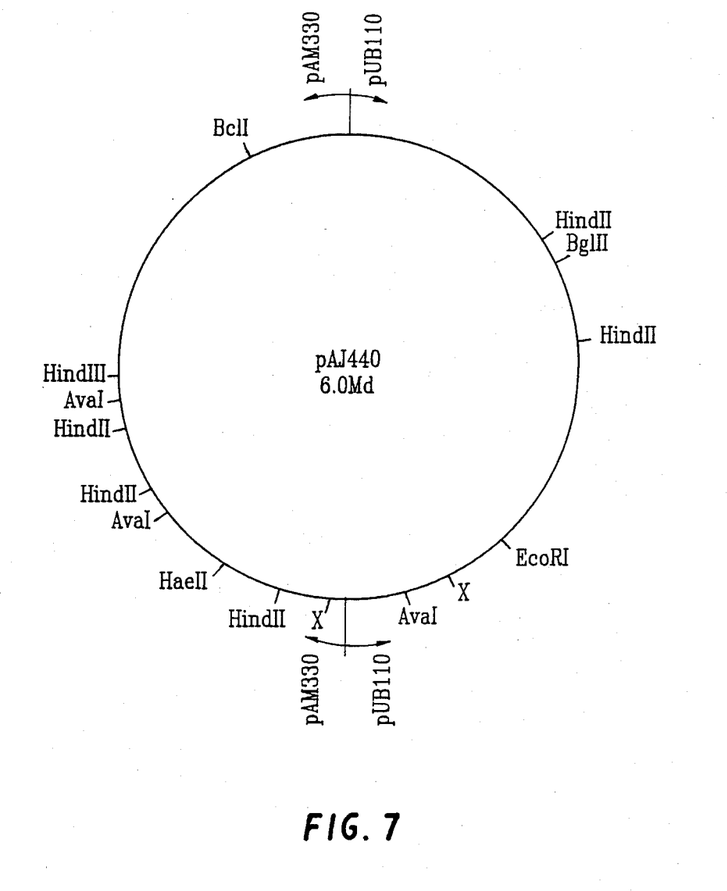
FIG. 7 shows a restriction map of composite plasmid pAJ 440.
Figure 8:
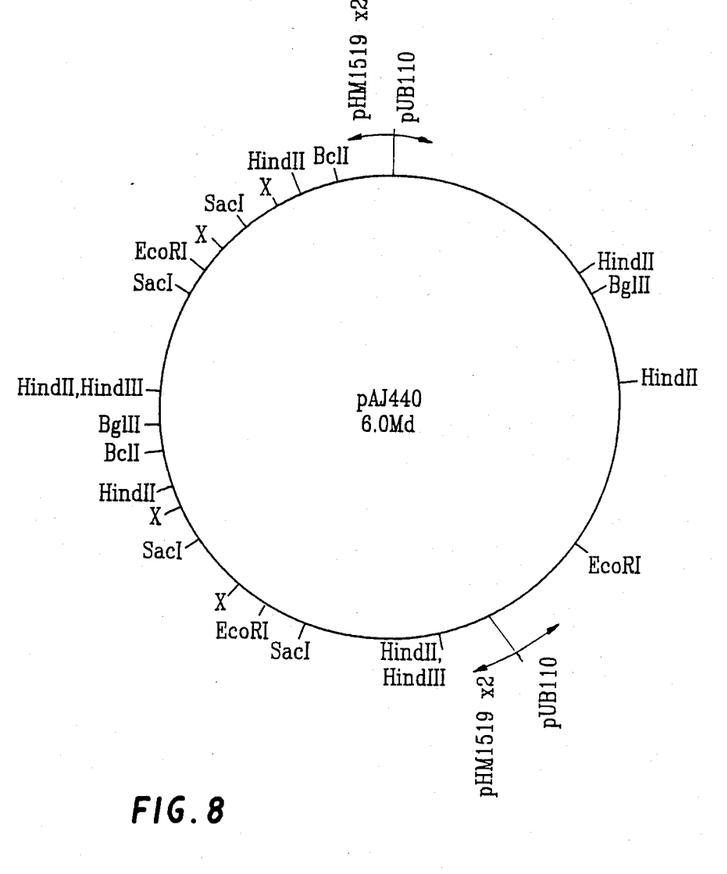
FIG. 8 shows a restriction map of composite plasmid pAJ 3148.

Among the examples of composite plasmids useful in the present invention are those present in hosts deposited at appropriate international depository authorities as follows:

pAJ 655:
  *Escherichia coli* AJ11882, FERM-BP 136, (FERM P6517);
  *Corynebacterium glutamicum* SR 8201 ATCC 39135 (restriction map in FIG. 4);
pAJ 611:
  *Escherichia coli* AJ 11884, FERM-BP 138 (FERM-P6519) (restriction map in FIG. 5);
pAJ 1844:
  *Escherichia coli* AJ 11883, FERM-BP 137 (FERM-P 8518); *Corynebacterium glutamicum* ATCC 39136 (restriction map in FIG. 6);
pAJ 440:
  *Bacillus subtilis* AJ 11901, FERM-BP 140 (restriction map in FIG. 7);
pAJ 3148:
  *Corynebacterium glutamicum* SR 8203 ATCC 39137 (restriction map in FIG. 8).

FERM-BP and PERM P identification numbers are identification numbers for cultures deposited with the Fermentation Research Institute, Agency of Industrial Science and Technology, Ministry of International Trade and Industry, 1-3, Higashi 1-Chome, Yatabe-Machi, Tsukuba-Gun, Ibaraki-Ken 305, Japan. ATCC identification numbers are identification numbers for cultures deposited at the American Type Culture Collection, 12301 Parklawn Drive, Rockville, Md. 20852, U.S.A.

The composite plasmids can be obtained from the cells of the microorganisms on deposit, by lysing the cells previously harvested at late exponential growth phase with lysozyme and SDS, adding polyethylene glycol to the supernatant obtained from the lysate by centrifugation at 30,000 xg, and purifying the precipitated DNA by fractionation using cesium chloride-ethidium bromide equilibrium density gradient centrifugation. The composite plasmids can also be expelled to obtain host strains without injury thereto from the deposited microorganisms by spontaneous loss or "curing" (Bacteriological Reviews, 36: 361–405 (1972)).

Insertion of the DAPDase gene into one of the appropriate replication vehicles can be done by restriction of the replication vehicle with appropriate endonuclease enzymes, and ligation of the appropriate gene sequence thereinto, as is well known in the art.

The incorporation of the vehicle carrying the DAPDase gene into the hosts of Coryneform bacteria can be done by treating the cells of the DNA recipient with calcium chloride to increase the permeability of DNA (as is reported regarding *E. coli* K-12 by Mandell, M et al, Journal of Molecular Biology, 53: 159 (1970)), or by incorporating at a specific stage of growth when cells become capable of incorporating DNA (as is reported for *Bacillus subtilis* by Duncan, C. H. et al, *Gene*, 153 (1977)). The plasmids can also be incorporated into the recipients by forming protoplasts or spheroplasts of the DNA recipients which easily incorporate plasmid DNA, as is known for *Bacillus subtilis*, Actinomycetes and yeast, and reported by Chang, S. et al, *Molec. Gen. Genet.* 168: 111 (1979), Bibb et al, *Nature*, 274: 398 (1978), Hinnen, A. et al, *PNAS USA*, 75: 1929 (1978)).

Since the composite plasmids transform the Coryneform bacteria into drug resistant bacteria, the transformants which contain the plasmids inserted with the DAPDase gene can be easily identified by testing their resistance to the drug. When vehicles having no genetic makers are used for the preparation of the recombinant DNA, auxotrophs for DAPDase are preferred as the hosts, since transformants carrying the vehicle inserted with the DAPDase can be easily distinguished from the host cells by testing their dap requirement for growth.

The DAPDase gene inserted in the composite plasmid can be transferred easily into another vehicle by conventional methods, if necessary.

The methods of culturing the L-lysine producing strains thus obtained are conventional, and are similar to the methods for the cultivation of known lysine producing microorganisms. The culture medium employed can be a conventional medium containing carbon sources, nitrogen sources, and inorganic ions and, when required, minor organic nutrients such as vitamins and amino acids. Examples of suitable carbon sources include glucose, sucrose, lactose, starch hydrolysate, and molasses. Gaseous ammonia, aqueous ammonia, ammonium salts and other nitrogen-containing materials can be used as the nitrogen source.

Cultivation of the transformed organisms containing the vehicle carrying the DAPDase gene is conducted under aerobic conditions in which the pH and the temperature of the medium are adjusted to a suitable level, and continued until the completion of formation of L-lysine.

The amino acid which accumulates in the culture medium can be recovered by conventional procedures.

By the methods of the present invention, L-lysine can be produced in higher yields than has been achieved in previously known methods using artificial mutants of Brevibacterium and Corynebacterium.

Having generally described this invention, a further understanding can be obtained by reference to certain specific examples which are provided herein for purposes of illustration only and are not intended to be limiting unless otherwise specified.

EXAMPLE 1

1. Preparation of chromosomal DNA from donor strain

Brevibacterium lactofermentum ATCC 13869 (wild type) was cultured at 30° C., in 1 l CM-2G medium of 1% yeast extract, 1% peptone, 0.5% glucose, 0.5% NaCl, and pH 7.2. From cells harvested at an exponential growth phase, 3.5 mg of chromosomal DNA was extracted by the conventional phenol method and used as the donor DNA which might had contained the diaminopimelic acid decarboxylase gene.

2. Preparation of vector plasmid DNA

Hybrid plasmid pAJ 1844 (FIG. 6) was constructed as a vector by combination of pHM 1519 (FIG. 3), a cryptic plasmid of Corynebacterium glutamicum ATCC 13058, and pBR 325, an artificial vector plasmid of Escherichia coli K-12. This new hybrid plasmid pAJ 1844 is a shuttle vector which propagates and expresses its chloramphenicol resistant marker in E. coli K-12, B.lactofermentum ATCC 39134 and C. glutamicum ATCC 13032.

80 μg of pAJ 1844 DNA was extracted and used as the vector DNA from B. lactofermentum ATCC 39134/pAJ 1844 cells grown in 100 ml CM-2G consisted of 1% yeast extract, 1% peptone, 0.5% NaCl and 0.5% glucose and of pH 7.0. Extraction of plasmid DNA was performed by lysozyme treatment, SDS treatment, agarose gel electrophoresis, and extraction from the gel.

Corynebacterium glutamicum ATCC 13058 and Escherichia coli C-600 both harboring pAJ 1844 have been deposited with numbers ATCC 39136 and FERM-BP 137.

3. Insertion of chromosomal DNA fragment into vector DNA

Ten micrograms of chromosomal DNA was partially digested with 5 units of endonuclease Pst I at 37° C. for 5 to 60 min. 10 μg of vector DNA was completely digested with Pst I. After inactivation of Pst I by heating, both DNAs were mixed and ligated with T4 ligase at 10° C. for 24 hr.

4. Cloning of the diaminopimelic acid decarboxylase (DAPDase) gene.

B. lactofermentum ATCC 39134 (lys−, thr−, met−) was used as a recipient strain for the cloning of DAP decarboxylase gene. By auxanography, one of the deficient steps was determined to be DAP decarboxylase on the lysine biosynthesis, since this mutant grew on L-lysine but did not on dap.

The protoplast transformation method was used for the introduction of the chimeric DNA described above into the recipient cells ATCC 39134.

At their early exponential growing phase in 5 ml CM-2G, the cells were treated with 0.6 unit/ml penicillin G for 1.5 hr, harvested, and washed with SMMP medium of 500 mM sucrose, 20 mM maleate, 20 mM $MgCl_2$, 3.5% Difco Penassay broth, and pH 6.5. Protoplasts were made from those cells by treatment with 10 mg/ml of lysozyme in SMMP medium at 30° C. for 20 hr. The cells were spun, washed with SMMP medium, and resuspended in 0.5 ml SMMP medium. This protoplast suspension was mixed with 5 μg chimeric DNA, incubated for 2 min. in the presence of 5 mM EDTA and 2% carboxymethyl cellulose, washed with SMMP, cultivated in SMMD at 30° C. for 2 hr. to allow for enough expression of chloramphenicol resistance and finally inoculated on a regeneration medium of 1.2% Tris, 0.05% KCl, 1% glucose, 0.81% $MgCl_2.6H_2O$, 0.22% $CaCl_2.2H_2O$, 0.4% peptone, 0.4% yeast extract, 0.1% casamino acid, 0.02% $K_2HPO_4$, 13.5% sodium succinate, 0.8% agar and 3 μg/ml chloramphenicol, pH 7.0.

After 2 weeks culture at 30° C., chloramphenicol resistant colonies which appeared on the plates were replicated on a minimal medium of 0.5% glucose, 0.15% $(NH_4)_2SO_4$, 0.15% urea, 0.1% $KH_2PO_4$, 0.01% $MgSO_4.7H_2O$, 0.0001% $CaCl_2.2H_2O$, 30 μg/l d-biotin, 100 μg/l thiamine·HCl, 500 μg/l L-threonine, 500 μg/l L-methionine and 1.5% agar, pH 7.0.

The colony which appeared was purified, confirmed for chloramphenicol resistance and lysine prototrophy, this transformant being designated as AJ 12031 and deposited as FERM BP-277.

5. Analysis of chimeric plasmid

Figure 9:
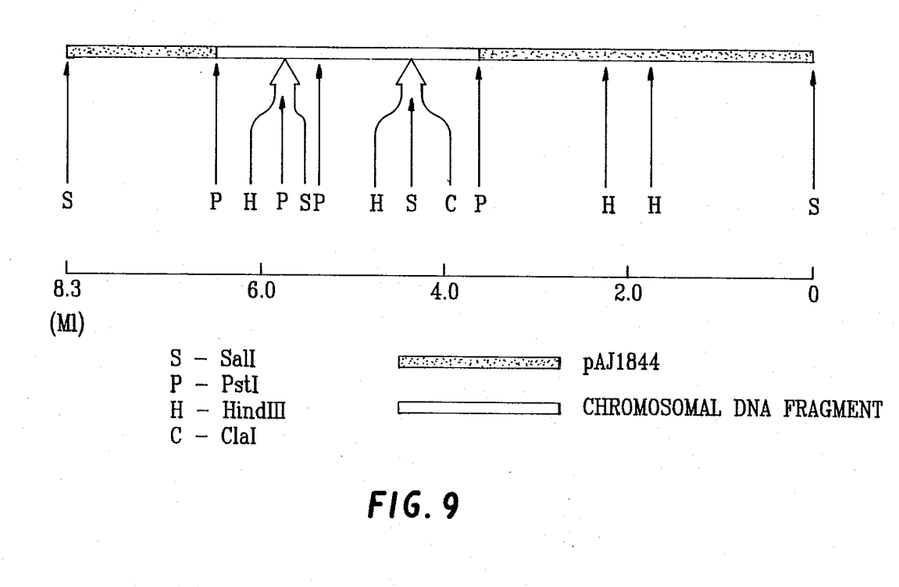
FIG. 9 shows a restriction map of plasmid pAJ 101.

Plasmid DNA was extracted from AJ 12031 by the same procedure described in Section 2. One microgram of this DNA was digested with Pst I and analysed by agarose gel electrophoresis. The chimeric plasmid designated as pAJ 101 was composed of 5.4 megadalton of pAJ 1844 and 2.9 megadalton of foreign DNA which carries the DAP decarboxylase gene. The 2.9 megadalton DNA was further cleaved by complete digestion with Pst I, Sal I and Hind III to 3 pieces, 1.9, 0.7 and 0.3 megadalton each; Cla I also cleaved this chromosomal DNA (FIG. 9).

6. DAP decarboxylase activity of transformants

B. lactofermentum AJ 12031 (FERM BP-277) as the transformant, ATCC 39134 as the recipient strain, and ATCC 13869 as the donor strain were all cultured overnight in CM-2G medium, harvested, washed, resuspended with 100 mM K-phosphate buffer (pH 7.5), sonicated, and centrifuged. The supernatants were used as crude enzyme solutions. The DAP decarboxylase reaction mixture was composed of 10% crude enzyme solution, 1 mg/ml of dap as enzyme substrate and 100 mM K-phosphate buffer (pH 7.5). After incubation at 37° C. for 3 hr, the reaction mixtures were applied to liquid chromatography to estimate the amounts of dap and lysine, as the reaction substrate and product. As shown in Table 1, the DAP decarboxylase of the transformant was about twice that of DNA donor strain.

TABLE 1

DAP Decarboxylase Activity of Transformant

| Strain | Role in this experiment | Lysine produced μmol/min/mg protein |
|---|---|---|
| B. lactofermentum AJ 12031, (FERM-BP-277) (lys+) | transformant | 15.8 |
| ATCC 39134 (lys−) | DNA recipient | 0.3 |
| ATCC 13869 (lys+) | DNA donor | 8.2 | lys+ = prototrophy depended on the gene existing on plasmid

7. Transformation of Lysine-producing strains by DAP-decarboxylase gene clone, pAJ 101

Two kinds of lysine-producing mutants; *B. lactofermentum* AJ 12019 (NRRL B-15346), a homoserine auxotrophic mutant, and AJ 3789 (FERM P-2647), a lysine-analog, S-(2-aminoethyl)-L-cysteine resistant mutant, were transformed by pAJ 101 DNA. After the confirmation of transformants by chloramphenicol resistancy and agarose-gel DNA analysis, AJ 12032 (AJ 12019 transformed by pAJ 101) and AJ 12033 (AJ 3789 transformed by pAJ 101) were selected as the representative transformants.

8. Lysine production by transformants

Transformants and other strains were examined for their lysine producing abilities by cultivation at 30° C., for 72 hr., in a synthetic medium of 10% glucose, 4% (NH4)2SO4, 0.1% KH2PO4, 0.04% MgSO4·7H2O, 0.001% FeSO4·7H2O, 0.0007% MnCl2·4H2O, 300 μg/l of d-biotin, 200 μg/l thiamine·HCl, 0.2% soybean protein hydrolysate, 0.06% L-threonine, 0.02% L-methionine and 5% CaCO3, and pH 7.5. Lysine was estimated by HPLC. The results are shown in Table 2.

TABLE 2

Lysine Producing Ability of Transformants

| Strain | Plasmid | Lysine HCl (g/l) |
|---|---|---|
| B. lactofermentum AJ 12019 (NRRL B-15346) hse− | None | 12.5 |
| AJ 12032 (FERM BP-278) hse+ | pAJ 101 | 13.0 |
| B. lactofermentum AJ 3789 (FERM P-2647) AECr, CCL+, Ala− | None | 39.4 |
| AJ 12033 (FERM BP-279) AECr, CCL+, Ala− | pAJ 101 | 41.1 | hse− = homoserine auxotroph; AECr = S—2-aminoethyl-L-cysteine resistant; CCLr = α chlorocaprolactam resistant; Ala− = alanine auxotroph; hse+ = homoserine prototrophy

EXAMPLE 2

1. Transformation of *Corynebacterium glutamicum* by the chimeric plasmid pAJ 101

The chimeric plasmid pAJ 101 which carries the DAP decarboxylase gene was extracted from *B. lactofermentum* AJ 12031 (FERM-BP-277) by the method described in Example 1, section 2 and used for the transformation of *C. glutamicum* ATCC 13287, a homoserine auxotroph, by the method described in Example 1, section 4. The transformant was selected by chloramphenicol resistance, designated as SR 8301 and deposited as NRRL B-15348.

2. Lysine production by Transformant

Cultivation was carried out as described in Example 1, section 8. The result is shown in Table 3.

TABLE 3

Lysine-producing Abilty of Transformant

| Strain | Plasmid | Lysine HCl (g/l) |
|---|---|---|
| C. glutamicum ATCC 13287, Hse− | None | 8.0 |
| SR 8301 (NRRL B-15348) Hse+ | pAJ 101 | 8.5 |

What is claimed as new and intended to be covered by Letters Patent of the United States is:

1. A bacterium comprising a Coryneform host containing an expression vehicle comprising a genetic sequence obtained from a Coryneform bacterium and comprising information coding for the production of diaminopimelic acid decarboxylase, said bacterium producing a greater amount of lysine than said host under identical conditions,
   wherein said Coryneform host comprises at least one member selected from the group consisting of *Brevibacterium saccarolyticum* ATCC 14066, *Brevibacterium immariophilum* ATCC 14068, *Brevibacterium lactofermentum* ATCC 13869, *Brevibacterium lactofermentum* ATCC 39134, *Brevibacterium roseum* ATCC 13825, *Brevibacterium flavum* ATCC 13826, and *Corynebacterium acetoacidophilum* ATCC 13870;
   wherein said information coding for the production of diaminopimelic acid decarboxylase is obtained from *Brevibacterium lactofermentum* ATCC 13869 (wild type); and
   wherein said expression vehicle is obtained from at least one member selected from the group consisting of *Corynebacterium glutamicum* FERM-P 5484, *Escherichia coli* FERM-BP 136, *Corynebacterium glutamicum* ATCC 39135, *Escherichia coli* FERM-BP 138, *Escherichia coli* FERM-BP 137, *Corynebacterium glutamicum* ATCC 39136, *Bacillus subtilis* FERM-BP 140, and *Corynebacterium glutamicum* ATCC 39137.

2. The bacterium of claim 1, wherein said information coding for the production of diaminopinelic acid decarboxylase is a DNA fragment which has a molecular weight of about 2.9±0.1 megadaltons, having two Pst I, two Sac I, two Hind III, one Cla I restriction endonuclease sites, and is flanked by two Pst I sites.

3. The bacterium of claim 1, wherein said Coryneform host is mutated to a lower restriction enzyme activity prior to being used as a host.

4. The bacterium of claim 1, wherein said host is a homoserine auxotroph.

5. The bacterium of claim 1, wherein said host is resistant to S-(2-aminoethyl)-cysteine.

6. A method for producing L-lysine by fermentation, which comprises:
   culturing in an appropriate medium a bacterium comprising a Coryneform host containing an expression vehicle comprising a genetic sequence obtained from a Coryneform bacterium and comprising information coding for the production of diaminopimelic acid decarboxylase, said bacterium producing a greater amount of lysine than said host under identical conditions.
wherein said Coryneform host comprises at least one member selected from the group consisting of *Brevibacterium saccarolyticum* ATCC 14066, *Brevibacterium immariophilum* ATCC 14068, *Brevibacterium lactofermentum* ATCC 13869, *Brevibacterium lactofermentum* ATCC 39134, *Brevibacterium roseum* ATCC 13825, *Brevibacterium flavum* ATCC 13826, and *Corynebacterium acetoacidophilum* ATCC 13870;
wherein said information coding for the production of diaminopimelic acid decarboxylase is obtained from *Brevibacterium lactofermentum* ATCC 13869 (wild type); and
wherein said expression vehicle is obtained from at least one member selected from the group consisting of *Corynebacterium glutamicum* FERM-P 5484, *Escherichia coli*, FERM-BP 136, *Corynebacterium glutamicum* ATCC 39135, *Escherichia coli* FERM-BP 138, *Escherichia coli* FERM-BP 137, *Corynebacterium glutamicum* ATCC 39136, *Bacillus subtilis* FERM-BP 140, and *Corynebacterium glutamicum* ATCC 39137; and
recovering L-lysine from said medium.

7. The method of claim 6, wherein said information coding for the production of diaminopimelic acid decarboxylase is a DNA fragment which has a molecular weight of about 2.9±0.1 megadaltons, two Pst I, two Sac I, two Hind III, one Cla I restriction endonuclease sites, and is flanked by two Pst I sites.

8. A Coryneform bacterium which is selected from the group consisting of those having the identifying characteristics of FERM BP-277, FERM BP-278, NRRL B-15348 and FERM BP-279.

9. The bacterium of claim 8 which is NRRLL B-15348.

* * * * *